United States Patent [19]

Balzer et al.

[11] Patent Number: 5,282,987
[45] Date of Patent: * Feb. 1, 1994

[54] CARBOXY ETHERS

[75] Inventors: Dieter Balzer, Haltern; Heinz Riemer, Bottrop; Werner Friedrich, Herten, all of Fed. Rep. of Germany

[73] Assignee: Huels Aktiengesellschaft, Marl, Fed. Rep. of Germany

[*] Notice: The portion of the term of this patent subsequent to Nov. 26, 2008 has been disclaimed.

[21] Appl. No.: 740,460

[22] Filed: Aug. 5, 1991

Related U.S. Application Data

[63] Continuation-in-part of Ser. No. 450,090, Dec. 13, 1989, Pat. No. 5,068,422.

[30] Foreign Application Priority Data

Feb. 8, 1989 [DE]  Fed. Rep. of Germany ....... 3903663

[51] Int. Cl.$^5$ ................ C10M 129/32; C10M 145/36
[52] U.S. Cl. ....................... 252/34; 252/39; 252/41; 252/49.003; 252/49.005; 252/173; 252/306; 562/587; 560/186
[58] Field of Search .......... 562/587; 560/186; 252/56 S, 34, 56 R, 49.3, 49.5, 39, 41, 173, 306

[56] References Cited

U.S. PATENT DOCUMENTS

| | | | |
|---|---|---|---|
| 2,803,646 | 8/1957 | Bell, Jr. et al. | 560/186 |
| 4,214,101 | 7/1980 | Miya et al. | 562/587 |
| 4,759,931 | 7/1988 | van Paassen | 562/587 |
| 4,766,153 | 8/1988 | Casciani | 562/587 |
| 5,068,422 | 11/1991 | Balzer et al. | 562/587 |

*Primary Examiner*—Jacqueline V. Howard
*Attorney, Agent, or Firm*—Oblon, Spivak, McClelland, Maier & Neustadt

[57] ABSTRACT

A carboxy ether of formula (II):

$$[R-O(C_3H_6O)_x(C_2H_4O)_y(C_3H_6O)_z]_2CHCOOM \qquad (II)$$

is disclosed. In formula (II) R is (i) a saturated or unsaturated, linear or branched group containing 6 to 20 carbon atoms, (ii) an alkylaromatic group or an alkylcycloaliphatic group, each containing a total of 4 to 16 carbon atoms in its alkyl group, (iii) a dialkylaromatic, dialkylcycloaliphatic, or trialkylcycloaliphatic group, each containing a total of 5 to 24 carbon atoms in its alkyl groups, or (iv) a trialkylaromatic group with a total of 7 to 28 carbon atoms in its alkyl groups; x is 0 to 15, y is 1 to 40, z is 0 to 15; and M is an alkali metal cation, an alkaline earth metal cation, an ammonium cation, an alkanolammonium cation, or a proton.

13 Claims, No Drawings

CARBOXY ETHERS

This is a continuation-in-part of U.S. patent application 07/450,090, filed Dec. 13, 1989, now U.S. Pat. No. 5,068,422.

BACKGROUND OF THE INVENTION

1. Field of the Invention

The invention relates to carboxy ethers, to methods for their manufacture, and to their uses.

2. Discussion of the Background

Carboxy ethers of formula (I)

$$[R-O(CH_2-CH_2)_n-CH_2COO]_m M^{m+} \quad (I)$$

where R is a hydrophobic group, n is a number ordinarily between 1 and 100, and M is a hydrogen or an ammonium ion, or a monovalent or multivalent cation of valence m, have been known for a long time (U.S. Pat. No. 2,183,853). These carboxy ethers are used as surfactants in the areas of:

(i) washing and cleaning agents (Schulze, K., 1975, *Seifen. Oele. Wachse.* 101:37);
(ii) petroleum recovery (Blazer, D. 1983, *Oil Gas European Magazin.* 1:50); and
(iii) emulsification (as emulsifiers), in relation to metal treatment (Friedrich, W., and Riemer, H., 1988, *Chemische Industrie.* 4:49).

These carboxy ethers can be produced by reacting the corresponding hydroxyethoxy compounds with chloroacetates or chloroacetic acid, in the presence of an alkali (Ger. Pat. 2,418,444), or by catalytic oxidation via oxygen (Ger. OS 28 16 127), hydrogen peroxide (Eur. OS 0 039 111), or butyl peroxide (Eur. OS 0 001 868), typically with palladium.

Aqueous solutions of these carboxy ethers have however only low viscosities. There is however a need for carboxy ethers which form high viscosity aqueous solutions.

SUMMARY OF THE INVENTION

Accordingly, it is an object of this invention to provide carboxy ethers which form high viscosity aqueous solutions.

The inventors have now discovered carboxy ethers which satisfy this object and other objects of this invention which will become apparent from the description of the invention given herein below. The present invention provides carboxy ethers of formula (II):

$$[R-O(C_3H_6O)_x(C_2H_4O)_y(C_3H_6O)_z]_2 CHCOOM \quad (II)$$

wherein:

R is (i) a saturated or unsaturated linear or branched $C_{6-20}$ alkyl group,
(ii) an alkylphenyl group or an alkylcycloaliphatic group, each containing 4 to 16 carbon atoms in the alkyl group;
(iii) a dialkylphenyl, dialkylcycloaliphatic, or trialkylcycloaliphatic group, each containing a total of 5 to 24 carbon atoms in the alkyl groups; or
(iv) a trialkylphenyl group containing a total of 7 to 28 carbon atoms in the alkyl groups;

x is 0 to 15; y is 1 to 40; z is 0 to 15; and

M is an alkali- or alkaline earth metal cation, an ammonium cation, a $C_{1-4}$ alkanolammonium cation, or a proton.

DETAILED DESCRIPTION OF THE PREFERRED EMBODIMENTS

In distinction from the known carboxy ethers (carboxymethylated hydroxyethoxy compounds, or carboxymethylated alkoxy compounds) of formula (I), the compounds of formula (II) may be referred to as bis(alkylphenolalkoxy)acetic acids, or bis(alkylcyclo-hexyloxyalkoxy) acetic acids, or bis(hydroxypolyalkoxy)acetic acids.

The compounds of formula (II) are manufactured by reacting the corresponding alkoxy compounds with dichloroacetic acid in the presence of alkali at elevated temperature and reduced pressure.

The reduced pressure serves to remove most of the water produced as a reactant or fed with the alkali. By-products, in addition to a small amount of water, include the chloride of the alkali cation (in an approximately stoichiometric amount), and residual alkoxy compound (since the alkoxy compound is not quantitatively converted, as a rule).

Conversions of 90% or above (based on the alkoxy compound) are not unusual. In many applications it is not necessary to separate out the alkali chloride. However, if this is desired, the reaction mixture may be acidified, e.g. with a strong acid under heating, to bring about a separation into an organic upper phase containing the free alkoxyacetic acid compound and an aqueous lower phase, wherewith the upper phase may be readily isolated.

In this operation the carboxy ether hydrolyzes only to a relatively small extent; this is completely unexpected, in view of the acetal structure. The acid is then converted into a desired salt by a base.

In the case of alcohols or alkylphenols, or alkylcyclohexanols, having relatively low carbon numbers (<8 in the case of alcohols, and in the case of alkylphenols), or at very high degrees of ethoxylation (>15 to 25, depending on the length of the hydrophobic group), phase separation is less suitable for separating out the alkali chloride, and may not even occur. In such cases the reaction products can be extracted with ether or other organic solvents in which alkali chlorides are insoluble or only slightly soluble.

If the boiling point is not too high, separation of unconverted alkoxy compounds can be accomplished in simple fashion by distillation. In most application situations, such a separation is unnecessary.

Critical parameters of the production reaction are the temperature, the pressure, and most importantly the amount of dichloroacetic acid. High degrees of conversion require a substantial excess of dichloroacetic acid. Suitable molar ratios of dichloroacetic acid to alkoxy compound which may be used are in the range 1.1:1 to 3:1, particularly 1.3:1 to 1.8:. Suitable reaction temperatures are preferably slightly below the boiling conditions for the alkoxy compound, in the range 60° to 180° C., particularly between 80° and 140° C. The reaction pressure should be between 1 and 300 mbar, preferably between 5 and 100 mbar.

Candidate compounds which can be converted include:

(i) Alkxy compounds of saturated or unsaturated, straight chain or branched alcohols containing 6 to 20 carbon atoms;

(ii) Alkoxy compounds of alkylphenols and alkylcyclohexanols in which the alkyl groups on the phenol or cyclohexanol are saturated or unsaturated, straight chain or branched and contain from 4 to 16 carbon atoms;

(iii) Alkoxy compounds of dialkylphenols and dialkylcyclohexanols in which the alkyl groups on the phenol or cyclohexanol are saturated or unsaturated, straight chain or branched and have a total of 5 to 24 carbon atoms; and (iv) Alkoxy compounds of trialkylphenols and trialkylcyclohexanols in which the alkyl groups on the phenol or cyclohexanol are saturated or unsaturated, straight chain or branched and have a total of 7 to 28 carbon atoms.

The term "alkoxy compounds" used herein is understood to include reaction products of alcohols or alkylphenols or alkylcyclohexanols with ethylene oxide and/or propylene oxide, according to formula (III)

$$R\text{---}O(C_3H_6O)_x(C_2H_4O)_y(C_3H_6O)_zH, \qquad (III).$$

In formula (III) R represents a saturated or unsaturated linear or branched group containing 6 to 20, preferably 12 to 18, carbon atoms, an alkylaromatic or alkylcycloaliphatic group containing 4 to 16, preferably 8 to 12, carbon atoms in the alkyl group, a dialkylaromatic, dialkylcycloaliphatic, or trialkylcycloaliphatic group with a total of 5 to 24, preferably 8 to 18, carbon atoms in the alkyl groups, or a trialkylaromatic group with a total of 7 to 24, preferably 12 to 24, carbon atoms in the alkyl groups.

Variable x is 0 to 15, preferably 0 to 7; y is 1 to 40, preferably 2 to 20; and z is 0 to 15, preferably 0 to 7.

Dichloroacetic acid may be used in pure form or as a highly concentrated aqueous solution (c. 50-95 wt %). Alkali salts of dichloroacetic acid may be used instead of the acid, provided that they can be easily fed. The alkali used is usually NaOH or KOH or a mixture of these, in pulverized form or as a concentrated aqueous solution. 50% NaOH is preferred because it is easily fed.

Advantageously the reaction is carried out in a well stirred temperature-controlled vessel with suitable feed means. The operation may be discontinuous or continuous.

Ordinarily the alkoxy compound is initially charged into the vessel and the respective pipes for feeding the alkali and the dichloroacetic acid are immersed in the alkoxy compound. Most of the water drawn off can be condensed and separated out via an efficient condenser. If necessary, the remainder can be removed by cold traps or the like. Any organic material carried along can be separated out in a separator and returned to the reactor. When the addition of the components is completed, the reaction is already nearly complete. Thus, further stirring for only 1 to 2 hours is required.

The degree of conversion of the carboxy ether can be determined by 2-phase titration (as is commonly used for anionic surfactants). Safranin at pH 10 is used as the titrant.

Preferably, however, conversion is determined by analysis of the content of the alkoxy compound. For this, an isopropanol solution of the reaction product is first treated with an anionic ion exchanger, followed by a cationic ion exchanger, and the solvent is then removed to constant weight. The alkoxy compound content is determined by weighing. Correction for residual anionic surfactant can be made via a 2-phase titration.

In formula (II) variable M may be a $C_{1-4}$ alkyl ammonium cation. These $C_{1-4}$ alkyl groups may be methyl, ethyl, n-propyl, i-propyl, n-butyl, i-butyl, s-butyl, or t-butyl.

It has been discovered, surprisingly, in connection with the invention, that these compounds, in which two hydrophilic chains are linked together through the intermediary of a difunctional carboxylic acid, are in fact surface active, with much higher surface activity than the compounds of formula (I). For the same hydrophobic group and the same degree of ethoxylation, the values of the critical micelle concentration (CMC) are sometimes reduced by a factor of 10. CMC values of <10 ppm, such as are observed here, are extremely low among values known for anionic surfactants.

Surprisingly low values of surface tension at a water-Diesel oil interface were also measured. This result was directly confirmed by the good emulsifying action of the inventive carboxy ethers (see Example 6).

The present carboxy ethers are readily water soluble, given an adequate degree of ethoxylation. Ordinarily they are compatible with other nonionic, anionic, and cationic surfactants, and with water-soluble polymers, e.g. polyethylene oxide and polyvinyl alcohol.

The novel carboxy ethers have a property which is very uncommon among compounds according to formula (I) or other anionic surfactants. This is the property of forming relatively viscous aqueous solutions at low concentration of the surfactant (<10 wt. %), which solutions have high shear-stability. This suggests applicability in hydraulic fluids and lubricants.

Aqueous hydraulic fluids and lubricants are becoming increasingly important as a result of their low flammability and low environmental impact. They are generally comprised of:

water-soluble polymers such as, e.g., polyglycols,
pH regulators such as alkanolamines,
corrosion inhibitors such as, e.g., boric acid amine esters or sodium molybdate,
defoamers such as silicon compounds,
solubility promoters such as ethylene glycol, etc.

Suitable defoamers are disclosed in Kirk-Othmer, *Encyclopedia of Chemical Technology*, 3rd ed., Vol. 7, pp. 430-448, Wiley, NY (1979), which is incorporated herein by reference.

Polymers in particular provide the required viscosity to avoid losses due to leakage in the areas of gap seals in pumps and valves, and to form lubricating films between sliding solid surfaces. Studies have shown that the inventive carboxy ethers in combination with the above-mentioned other components of typical aqueous hydraulic fluids and lubricants in aqueous solution provide viscous, lubricating liquids.

Another important application for the inventive carboxy ethers is as surfactants in shampoos and other cleaning liquids. They may be used in particular in combination with other surfactants which are intended to have various degrees of foaming character (depending on the given application). Examples of suitable other surfactants include:

anionic surfactants such as, e.g., fatty alcohol sulfates, fatty alcohol ether sulfates, alkanesulfonates, alkylbenzenesulfonates, and olefinsulfonates, nonionic surfactants such as, e.g., fatty alcohol oxethylates, i.e. hydroxyethoxy derivatives of fatty alcohols, ROH+HOEtOX→HOEtOROH, and ethoxylated and nonethoxylated fatty acid sorbitan esters, amphoteric surfactants, and betaines (which are also amphoteric surfactants). The inventive carboxy ethers are also compatible with builders, bleaches, and extenders, which are common in detergents and the like, and thus the inventive compounds may be used advantageously with such components.

Suitable other surfactants, builders, bleaches, and extenders are disclosed in Kirk-Othmer, *Encyclopedia of Chemical Technology*, 3rd ed., Vol. 22, pp. 332-432, Wiley (1983), which is incorporated herein by reference.

In the case of a surfactant composition, the present carboxy ether is suitably present in an amount of 0.1-20 wt. %, preferably 1-10 wt. %. In the case of a washing and cleaning composition, the present carboxy ether is suitably present in an amount of 0.5-20 wt. %, preferably 2-10 wt. %. In the case of a hydraulic fluid composition, the present carboxy ether is suitably present in an amount of 3-25 wt. %, preferably 5-20 wt. %. In the case of a lubricant composition, the present carboxy ether is suitably present in an amount of 3-25 wt. %, preferably 5-20 wt. %.

Other features of this invention will become apparent in the course of the following descriptions of exemplary embodiments which are given for illustration of the invention and are not intended to be limiting thereof.

EXAMPLE 1

Into a cylindrical 2.5 liter stirred vessel equipped with double walls and a paddle stirrer, 970 g (2 moles) of (hydroxypolyethoxy)nonylbenzene with 6 moles of ethylene oxide per mole was charged, and then heated to 115° to 120° C. at c. 50 mbar. Then 20 g (1.6 moles) of dichloroacetic acid and 385 g (4.8 moles) of 50% sodium hydroxide were separately added to the reactor, via metering pumps, over a period of 2.5 hr. The water fed and the water produced in the reaction was condensed in a series of cold traps connected in series. Stirring under a vacuum was continued for 90 min. Analysis of the reaction product gave 10% residual content of the starting polyethoxy compound, water 0.2%, anionic surfactant 77%, and NaCl 14%. The corresponding degree of conversion was c. 90%.

EXAMPLE 2

(Hydroxypolyethoxy)nonylbenzene with 6 moles of ethylene oxide per mole was reacted with dichloroacetic acid by a method similar to that outlined in Example 1, with variation of some of the method parameters such as molar ratio of reactants, temperature, and reaction pressure. (Note that temperature and pressure determine the water concentration.) As seen from Table 1, conversion is favored by a high ratio of dichloroacetic acid to the hydroxypolyethoxy compound, and by sufficiently high temperature and sufficiently low pressure

EXAMPLE 3

Using the method outlined in Example 1, 865 g (1.1 moles) of hydroxypolyethoxydinonylphenol with 10 moles ethylene oxide per mole was reacted with 114.5 g (0.88 moles) of dichloroacetic acid and 211 g (2.64 moles) of 50% NaOH at 115° C. and 40 mbar, for 2 hr. After an additional stirring time of 1 hr under vacuum (40 mbar), anionic surfactant (71%), nonionic surfactant (20%)., and NaCl (9%) were determined Conversion was c. 78%.

TABLE 1

Conversion as a function of educt ratio, temperature, and reaction pressure, for hydroxypolyethoxy (nonylbenzene) with 6 moles of ethylene oxide per mole.

| | Molar Ratio of Hydroxypolyethoxy Compound to Acid | P (mbar) | T (°C.) | Conversion (%) |
|---|---|---|---|---|
| a | 2:1 | 20 | 95 | 27 |
| b | 2:1 | 20 | 115 | 57 |
| c | 2:1.3 | 20 | 115 | 75 |
| d | 2:1.6 | 20 | 115 | 83 |
| e | 2:1.6 | 10 | 115 | 84 |
| f | 2:1.6 | 40 | 115 | 87 |
| g | 2.4:1 | 40 | 115 | 48 |
| h | 2:1.6 | 60 | 115 | 80 |
| i | 2:1.6 | 90 | 115 | 59 |

EXAMPLE 4

Using the method outlined in Example 1, 961 g (2.0 moles) of Alfol 1214 of hydroxypolyethoxy compound with 6 moles of ethylene oxide per mole was reacted with 209 g (1.6 moles) of dichloroacetic acid and 385 g (4.8 moles) of 50% NaOH at 115° to 120° C. and 40 mbar, for c. 2 hr. After an additional stirring time of 1 hr under vacuum, anionic surfactant (71%), nonionic surfactant (14%), and NaCl (14%) were determined. Conversion was c. 83%.

To separate out the NaCl and produce the acid, the reaction product was charged to a heatable vessel equipped with a stirrer and a drain cock, heated to c. 60° C., and an approximately equal volume of 10% sulfuric acid was added dropwise as rapidly as possible, under stirring. As soon as the phase separation was noticeable (within a few minutes as a rule), the stirrer was shut off and the phase separation was allowed to take place. The aqueous (lower) phase was removed. Analysis of the upper phase gave a content of nonionic surfactant of 18%, anionic surfactant 61%, water 20%, and NaCl 0.2%. The conversion had thus fallen to 78%, indicating that the carboxy ether has a tendency to hydrolyze (but the degree of hydrolysis is surprisingly small). This tendency can be minimized by minimizing temperature and conducting the phase separation rapidly, possibly with the aid of a centrifuge.

EXAMPLE 5

This Example demonstrates the high surface activity of the present carboxy ethers in comparison to the carboxymethylated ethoxy compounds of formula (I).

Table 2 shows the values of the surface tension measurements which then lead to determination of the CMCs for both structures based on the (polyethoxy)nonylbenzene with 6 mol ethylene oxide per mole, both being substantially NaCl-free sodium salts produced under comparable conversion (c. 90%).

TABLE 2

Surface tensions at 20° C. (ring tensiometer) of carboxy ethers, as a function of the surfactant concentration, in aqueous solution.

| Concentration (g/l) | (mN/m) | |
|---|---|---|
| | Formula (I) | Formula (II) |
| 0.001 | — | 41.5 |
| 0.0025 | 57 | 38.5 |
| 0.005 | 52 | 35.5 |
| 0.01 | 46 | 33 |
| 0.05 | 34 | 33 |
| 0.1 | 32 | 33 |

TABLE 2-continued

Surface tensions at 20° C. (ring tensiometer) of carboxy ethers, as a function of the surfactant concentration, in aqueous solution.

| Concentration | (mN/m) | |
|---|---|---|
| (g/l) | Formula (I) | Formula (II) |
| 0.25 | 33 | — |

The values of the CMCs resulting from the surface tension characteristics were 7.5 ppm for the inventive carboxy ether (formula (II)), and 60 ppm for the known carboxy ether (formula (I)).

EXAMPLE 6

This example demonstrates the high interfacial activity of the present carboxy ethers. With the aid of a spinning drop tensiometer (Site 04®, supplied by Kruess, of Hamburg), the interfacial tension of diesel oil/VE water with 0.2% nonylphenyl carboxy ether with 4 mol ethylene oxide per mole was measured, at temperatures of 20°–40° C. The surface tension was very low, at 0.08–0.1 mN/m.

A corresponding emulsion test carried out (with Diesel oil and 2% emulsifier in water) produced a finely divided blush-colored emulsion of high stability.

EXAMPLE 7

This example demonstrates the surprisingly high viscosity of aqueous solutions of the present carboxy ethers in comparison to compounds of formula (I). An example is nonylphenyl carboxy ether with 6 moles of ethylene oxide per mole and a conversion of 80%, dissolved in VE water. Because the solutions of the inventive carboxy ethers have strong structural viscosity at slightly higher concentrations, the viscosity data are based on shear rate c. 100 sec$^{-1}$ (see Table 3). If high shear forces are applied to solutions of the inventive carboxy ethers, as occurs, e.g., with ultrasound or with high rpm stirrers, the viscosity persists and does not degrade. In contrast to polymer solutions, the present compounds are shear stabile and in general may be used where an aqueous system is desired which has high viscosity under high shear stress.

TABLE 3

Viscosities (D = 100 sec$^{-1}$) of carboxy ethers in aqueous solution at 50° C.

| Concentration | (mPa.s) | |
|---|---|---|
| (g/l) | Formula I | Formula II |
| 3 | (0.5) | 1 |
| 5 | 1 | 45 |
| 7 | 1.4 | 270 |
| 10 | 2 | |

EXAMPLE 7

Hydraulic Fluid

A 15 wt. % solution of oleyl ether carboxylate triethanolammonium salt in water, having 7 mol ethylene oxide per mol, was prepared. The viscosity behavior of the solution at 50° C., shear region 10–300 sec$^{-1}$, is newtonian, with value 40 mPa-sec. A 10 minute ultrasound exposure (Telsonic VSG 1000, 20 kHz) did not change the viscosity and confirmed the shear stability of the system. The clear point of the solution is at 6° C. The solution does not experience changes with increasing temperature, up to 70° C. The frictional wear behavior (lubricating action) of the solution wa studied using a Reichert-type frictional wear weighing device, which measures the loss in weight of the test rolls after a 100 m friction run at load 1.5 kg. The mean value from 3 test runs was 9±1 mg at a specific moisture pressure of 2400 N/sq cm. A comparison test of wear using VE water gave a weight loss of 74 mg under analogous conditions, thereby demonstrating the favorable effect of the surfactant solution.

EXAMPLE 8

Manual Washing Agent

For testing the washing agent action, the mini-disk test was used (see Anstett, R. M., and Schuck, E. J., 1966 *JAOCS*, 43, 576). Here watch glasses smeared with fat or the like are manually cleaned at elevated temperature with a paintbrush, in the surfactant solution. The test conditions (preparations, geometries, amounts and concentrations of substances, temperatures, temperature gradients, and times) are precisely defined. The test was performed by several people, and it provided results which were reproducible. The number of watch glasses which can be cleaned is indicated by the disappearance of the foam. The soil employed was lard, applied to the watch glasses at 50.0° C. followed by a defined cooling process to 23° C. (room temperature). The initial washing temperature was also 50° C.

Detergent formulations as follows were prepared:

10 wt. % of C12–C14 fatty alcohol ether carboxylate with 6 mol ethylene oxide per mol, plus 5 wt. % of C13–C-17 alkanesulfonate; and 8 w. % of C1214 C14 fatty alcohol ether carboxylate with 6 mol ethylene oxide per mol, plus 7 wt. % of C11–C13 alkanesulfonate. These were tested for their cleaning action. At surfactant concentrations of 0.075 g/L, the number of watch glasses which could be cleaned was 15 and 14, respectively. This compares with only 13 watch glasses cleanable with ordinary detergents available on the market, which demonstrates the excellent cleaning properties of surfactant preparations based on the novel carboxy ethers.

EXAMPLES 9 and 10

Cooling Lubricants

Cooling lubricants which can be formulated with the inventive carboxy ethers include pure mineral-oil-based lubricants and also so-called "semisynthetic biostabile" lubricants.

Isononylphenol ether acetic acid, neutralized with oleylamine and accompanied by bis (isononylphenol polyglycol ether) acetate having 8 mol ethylene oxide per mol and wherein the polyglycol ether part is comprised of (on the average) 8 mol ethylene oxide, is suitable for use, e.g., as an emulsifier for paraffinic and naphthenic base-oils (e.g. "Energol WT 61" manufactured by BP, and "Coray 12" manufactured by Esso).

EXAMPLE 10

An emulsion concentrate based on a mineral oil:

75 parts by weight (pbw) base-oil ("Coray 12" or "Energol WT 61").

15 pbw emulsifier, viz. bis(alkylphenol+8 ethylene oxide)-acetic acid neutralized with oleylamine.

9 pbw corrosion protection agent (e.g., MAR-LOWET® 5459, supplied by Huels AG).

1 pbw conventional commercially available biocides and defoamants (0.5 pbw each).

EXAMPLE 11

A semisynthetic emulsion concentrate:

48 pbw Coray 12.
19 pbw monoethyl boric acid ester (see Huebner, J., 1990 *Mineraloeltechnik*, 6, June 1990, 1-31).
7.0 pbw MARLOWET® 1072 (supplied by Huels AG).
6.0 pbw bis(isononylphenol+6 ethylene oxide)-acetic acid.
10 pbw MARLOWET® 5459 (supplied by Huels AG).
9 pbw 1,2-propylene glycol.
1 pbw conventional commercially available biocides and defoamants (0.5 pbw each).

From this concentrate one can prepare a nearly transparent, stabile 2-3% emulsion with drinking water, which emulsion is usable as a cooling lubricant.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A carboxy ether of formula (II):

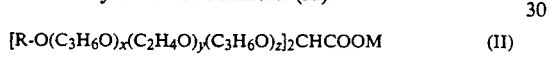

$$[R\text{-}O(C_3H_6O)_x(C_2H_4O)_y(C_3H_6O)_z]_2CHCOOM \qquad (II)$$

wherein:
R is (i) a saturated or unsaturated, linear or branched $C_{6\text{-}20}$-alkyl group; (ii) a phenyl group substituted with a $C_{4\text{-}16}$-alkyl group or a cycloaliphatic group substituted with a $C_{4\text{-}16}$-alkyl group; (iii) a dialkylphenyl group, wherein the total number of carbon atoms in the alkyl groups is 5 to 24, a dialkylcycloaliphatic group, wherein the total number of carbon atoms in the alkyl groups is 5 to 24, or a trialkylcycloaliphatic group, wherein the total number of carbon atoms in the alkyl groups is 5 to 24; or (iv) a trialkylphenyl group, wherein the total number of carbon atoms in the alkyl groups is 7 to 28;

x is 0 to 15, y is 1 to 40, z is 0 to 15; and
M is a $C_{1\text{-}4}$ alkanolammonium cation.

2. The carboxy ether of claim 1, Wherein R is said (i) saturated or unsaturated, linear or branched $C_{6\text{-}20}$ alkyl group.

3. The carboxy ether of claim 1, wherein R is said (ii) phenyl group substituted with a $C_{4\text{-}16}$-alkyl group or said cycloaliphatic group substituted with a $C_{4\text{-}16}$-alkyl group.

4. The carboxy ether of claim 1, wherein R is said (iii) dialkylphenyl group, said dialkylcycloaliphatic group, or said trialkycycloaliphatic group.

5. The carboxy ether of claim 1, wherein R is said (iv) trialkylphenyl group.

6. A surfactant composition comprising water and 0.1-20% by weight of a carboxy ether of formula (II):

$$[R\text{-}O(C_3H_6O)_x(C_2H_4O)_y(C_3H_6O)_z]_2CHCOOM \qquad (II)$$

wherein:
R is (i) a saturated or unsaturated, linear or branched $C_{6\text{-}20}$-alkyl group; (ii) a phenyl group substituted with a $C_{4\text{-}16}$-alkyl group or a cycloaliphatic group substituted With a $C_{4\text{-}16}$alkyl group; (iii) a dialkylphenyl group, wherein the total number of carbon atoms in the alkyl groups is 5 to 24, a dialkylcycloaliphatic group, wherein the total number of carbon atoms in the alkyl groups is 5 to 24, or a trialkylcycloaliphatic group, wherein the total number of carbon atoms in the alkyl groups is 5 to 24; or (iv) a trialkylphenyl group, wherein the total number of carbon atoms in the alkyl groups is 7 to 28;

x is 0 to 15, y is 1 to 40, z is 0 to 15; and
M is an alkali metal cation, an alkaline earth metal cation, an ammonium cation, a $C_{1\text{-}4}$ alkanolammonium cation, or a proton.

7. The surfactant composition of claim 6, further comprising another surfactant selected from the group consisting of anionic surfactants, nonionic surfactants, amphoteric surfactants and betaines.

8. A washing and cleaning composition, comprising water and 0.5-20% by weight of a carboxy ether of formula (II):

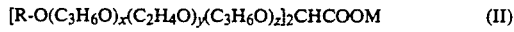

$$[R\text{-}O(C_3H_6O)_x(C_2H_4O)_y(C_3H_6O)_z]_2CHCOOM \qquad (II)$$

wherein:
R is (i) a saturated or unsaturated, linear or branched $C_{6\text{-}20}$-alkyl group; (ii) a phenyl group substituted with a $C_{4\text{-}16}$-alkyl group or a cycloaliphatic group substituted with a $C_{4\text{-}16}$alkyl group; (iii) a dialkylphenyl group, wherein the total number of carbon atoms in the alkyl groups is 5 to 24, a dialkylcycloaliphatic group, wherein the total number of carbon atoms in the alkyl groups is 5 to 24, or a trialkylcycloaliphatic group, wherein the total number of carbon atoms in the alkyl groups is 5 to 24; or (iv) a trialkylphenyl group, wherein the total number of carbon atoms in the alkyl groups is 7 to 28;

x is 0 to 15, y is 1 to 40, z is 0 to 15; and
M is an alkali metal cation, an alkaline earth metal cation, an ammonium cation, a $C_{1\text{-}4}$ alkanolammonium cation, or a proton.

9. The washing and cleaning composition of claim 8, further comprising an ingredient selected from the group consisting of builders, bleaches, and extenders.

10. A hydraulic fluid composition, comprising water and 3-25% by weight of a carboxy ether of formula (II):

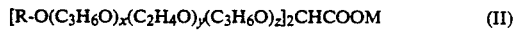

$$[R\text{-}O(C_3H_6O)_x(C_2H_4O)_y(C_3H_6O)_z]_2CHCOOM \qquad (II)$$

wherein:
R is (i) a saturated or unsaturated, linear or branched $C_{6\text{-}20}$-alkyl group; (ii) a phenyl group substituted with a $C_{4\text{-}16}$-alkyl group or a cycloaliphatic group substituted with a $C_{4\text{-}16}$alkyl group; (iii) a dialkylphenyl group, wherein the total number of carbon atoms in the alkyl groups is 5 to 24, a dialkylcycloaliphatic group, wherein the total number of carbon atoms in the alkyl groups is 5 to 24, or a trialkylcycloaliphatic group, wherein the total number of carbon atoms in the alkyl groups is 5 to 24; or (iv) a trialkylphenyl group, wherein the total number of carbon atoms in the alkyl groups is 7 to 28;

x is 0 to 15, y is 1 to 40, z is 0 to 15; and

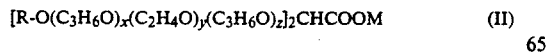

M is an alkali metal cation, an alkaline earth metal cation, an ammonium cation, a $C_{1-4}$ alkanolammonium cation, or a proton.

11. The hydraulic fluid composition, of claim 10, further comprising an ingredient selected from the group consisting of water-soluble polymers, pH regulators, corrosion inhibitors, defoamers, and solubility promoters.

12. A lubricant composition, comprising 3-25% by weight of a carboxy ether of formula (II):

$$[R-O(C_3H_6O)_x(C_2H_4O)_y(C_3H_6O)_z]_2CHCOOM \quad (II)$$

wherein:

R is (i) a saturated or unsaturated, linear or branched $C_{6-20}$-alkyl group; (ii) a phenyl group substituted with a $C_{4-16}$-alkyl group or a cycloaliphatic group substituted with a $C_{4-16}$-alkyl group; (iii) a dialkylphenyl group, wherein the total number of carbon atoms in the alkyl groups is 5 to 24, a dialkylcycloaliphatic group, wherein the total number of carbon atoms in the alkyl groups is 5 to 24, or a trialkylcycloaliphatic group, wherein the total number of carbon atoms in the alkyl groups is 5 to 24; or (iv) a trialkylphenyl group, wherein the total number of carbon atoms in the alkyl groups is 7 to 28;

x is 0 to 15, y is 1 to 40, z is 0 to 15; and

M is an alkali metal cation, an alkaline earth metal cation, an ammonium cation, a $C_{1-4}$ alkanolammonium cation, or a proton.

13. The lubricant composition of claim 12, further comprising an oil selected from the group consisting of parraffinic base oils and naphthenic base oils.

* * * * *